US008785688B2

(12) United States Patent
van Heiningen et al.

(10) Patent No.: US 8,785,688 B2
(45) Date of Patent: Jul. 22, 2014

(54) RECOVERY OF ACETIC ACID FROM WOOD EXTRACTS

(75) Inventors: Adriaan van Heiningen, Orono, ME (US); Herbert Sixta, Lenzing (AT); Byung-Hwan Um, Boothwyn, PA (US); Peter van Walsum, Orono, ME (US)

(73) Assignee: University of Maine System Board of Trustees, Bangor, ME (US)

( * ) Notice: Subject to any disclaimer, the term of this patent is extended or adjusted under 35 U.S.C. 154(b) by 1118 days.

(21) Appl. No.: 12/740,868

(22) PCT Filed: Oct. 31, 2008

(86) PCT No.: PCT/US2008/082119
§ 371 (c)(1),
(2), (4) Date: Jun. 27, 2011

(87) PCT Pub. No.: WO2009/059228
PCT Pub. Date: May 7, 2009

(65) Prior Publication Data
US 2011/0263895 A1   Oct. 27, 2011

Related U.S. Application Data

(60) Provisional application No. 61/001,141, filed on Oct. 31, 2007.

(51) Int. Cl.
*C07C 51/50* (2006.01)

(52) U.S. Cl.
USPC .......................................................... 562/608

(58) Field of Classification Search
None
See application file for complete search history.

(56) References Cited

U.S. PATENT DOCUMENTS

| 2,878,283 A | 3/1959 | Othmer et al. |
| 5,629,199 A | 5/1997 | Korfiatis et al. |
| 2007/0079944 A1 | 4/2007 | Amidon et al. |
| 2007/0219141 A1 | 9/2007 | Jones et al. |

OTHER PUBLICATIONS

Janvit Golob et al., Extraction of Acetic Acid from Dilute Aqueous Solutions with Trioctylphosphine Oxide, Ind. Eng. Chem. Process Des. Dev., 1981, pp. 433-435, vol. 20, Yugoslavia.
H.F. Al-Mudhaf et al., Partition Data of Acetic Acid Between Aqueous NaCl Solutions and Trioctylphosphine Oxide in Cyclohexane Diluent, Separation and Purification Technology, 2002, pp. 41-50, vol. 27 Kuwait.

*Primary Examiner* — Yevegeny Valenrod
(74) *Attorney, Agent, or Firm* — MacMillan, Sobanski & Todd, LLC

(57) ABSTRACT

In a process for recovering acetic acid from a wood extract, an aqueous wood extract is provided that contains acetic acid and dissolved hemicellulose containing uronic acid. A water insoluble solvent containing an extractant for the acetic acid is also provided. In a preferred embodiment, the solvent is undecane and the extractant is trioctylphosphine oxide. The wood extract is contacted with the solvent and extractant in order to extract the acetic acid from the wood extract. The acetic acid is then recovered from the solvent and extractant.

10 Claims, 4 Drawing Sheets

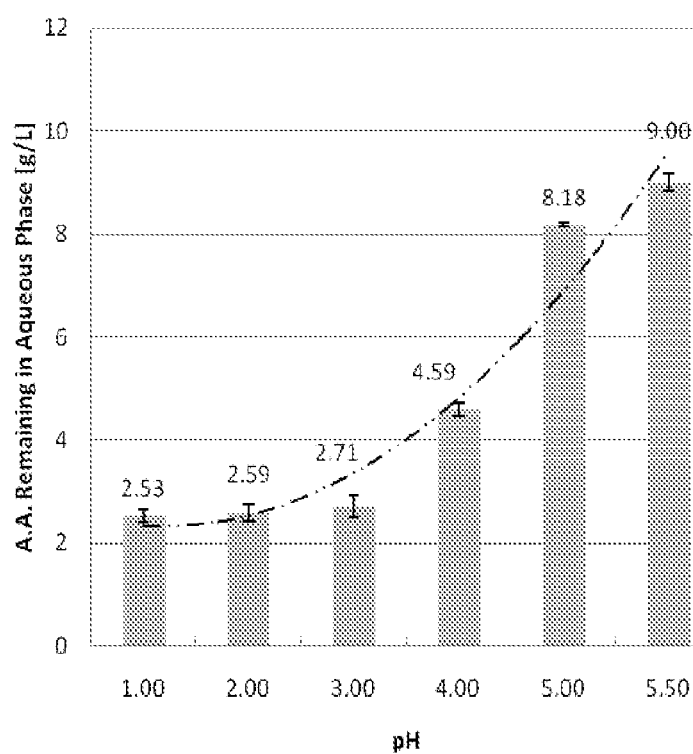
Figure 1. Acetic acid concentration in the aqueous phase as function of pH at 70°C. TOPO concentration of 37% (w/v). Initial concentration of acetic acid 10 g/L; reaction time 36 min.

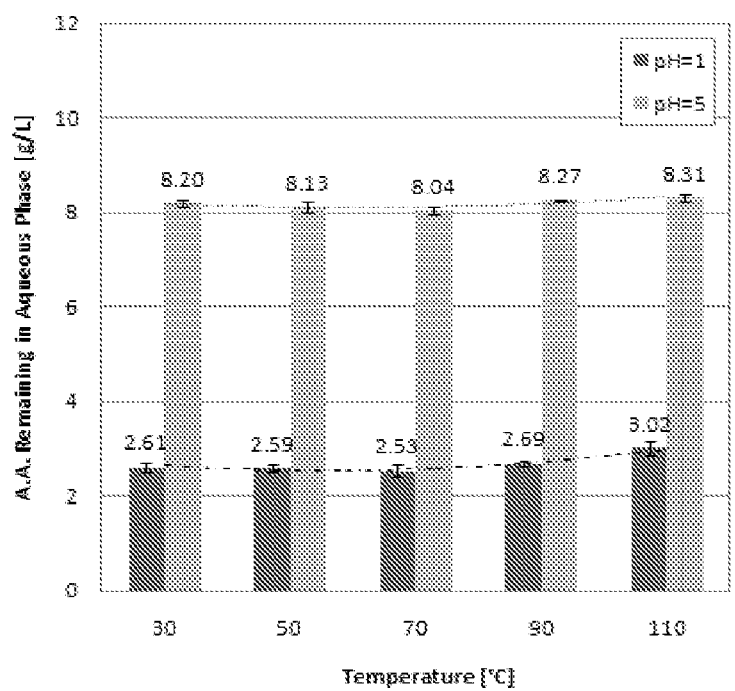
Figure 2. Acetic acid concentration in the aqueous phase as function of reaction temperature. TOPO concentration of 37 % (w/v); pH 1; Initial concentration of acetic acid 10 g/L; reaction time 36 min.

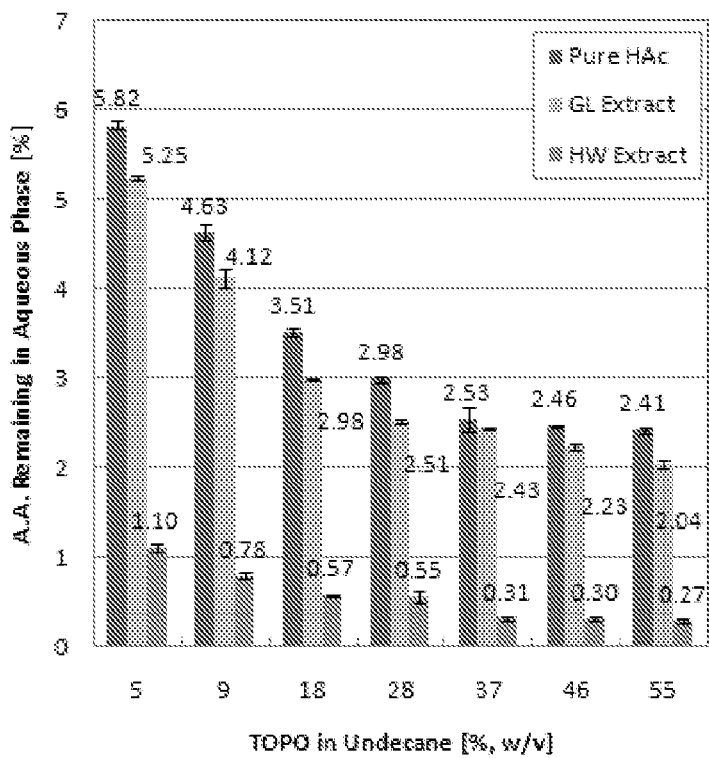
Figure 3. The extent of acetic acid extraction under various TOPO concentrations in undecane at pH=1 and 70°C; Initial concentration of pure acetic acid, GL extract, and HW extract solutions of 10, 8.32, and 1.27 g/L respectively; reaction time of 36 minutes.

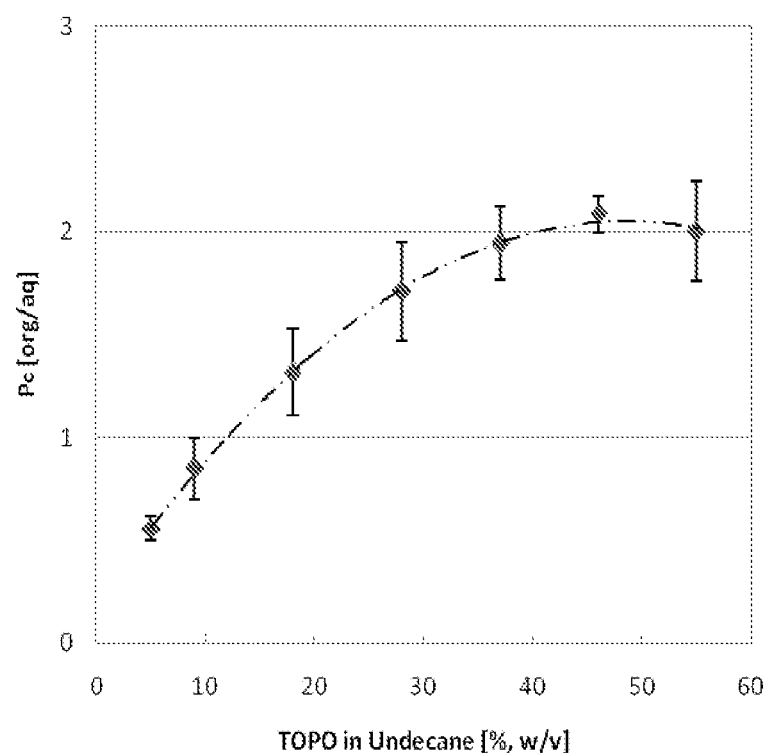
Figure 4. Partition coefficients ($P_c$) as function of TOPO concentrations in undecane for extraction of 10 g/L solution of pure acetic acid at pH 1 and 70 °C; reaction time 36 min.

RECOVERY OF ACETIC ACID FROM WOOD EXTRACTS

CROSS-REFERENCE TO RELATED APPLICATIONS

This application claims the benefit of U.S. Provisional Application No. 61/001,141, filed Oct. 31, 2007, the disclosure of which is incorporated herein by reference.

BACKGROUND OF THE INVENTION

This invention relates in general to the processing of wood products, and in particular to a process for recovering acetic acid from wood extracts.

Wood chips or lignocellulosic biomass are pretreated with high temperature steam/water or aqueous solutions to release sugars for fermentation purposes. In addition to sugars, compounds such as acetic acid/acetate and other organic acids or their conjugate base are also released. Because acetic acid is released in high quantities, and is both an inhibitor in fermentation processes of the sugars and has significant economic value as commodity chemical, it is advantageous to recover acetic acid from these solutions.

The use of trioctylphosphine oxide (TOPO), an extractant for removal of acids from aqueous solutions, is well known. Because of its high hydrogen bonding acceptor basisity, TOPO complexes strongly with a carboxylic acid when dissolved in water immiscible organic diluents such as undecane. In addition, TOPO is characterized by its excellent stability, high boiling point and low solubility in water.

The recovery of acetic acid from the evaporator condensate generated as part of multiple effect evaporation of acid sulfite waste pulping liquor using extraction by TOPO-undecane is practiced by Lenzing in Austria. In the Lenzing process, acetic acid and furfural are recovered at approximately 90%, further purified by distillation and then sold as final products.

Unlike the evaporator condensate used in the Lenzing process, wood extracts from wood chips or lignocellulosic biomass as described above contain dissolved sugars, uronic acids, formic acid or other organic acids. It would be expected that the acids would bind with TOPO, and as a result lead to deactivation of the extractant because the uronic and organic acids (except formic acid) are much less volatile than acetic acid and thus accumulate in the TOPO-undecane phase. Thus, it would be expected that a process similar to the Lenzing process would be unsuitable for the recovery of acetic acid from these wood extracts.

SUMMARY OF THE INVENTION

This invention relates to a process for recovering acetic acid from a wood extract. An aqueous wood extract is provided that contains acetic acid and dissolved hemicellulose containing uronic acid. A water insoluble solvent containing an extractant for the acetic acid is also provided. In a preferred embodiment, the solvent is undecane and the extractant is trioctylphosphine oxide. The wood extract is contacted with the solvent and extractant in order to extract the acetic acid from the wood extract. The acetic acid is then recovered from the solvent and extractant.

Various aspects of this invention will become apparent to those skilled in the art from the following detailed description of the preferred embodiment, when read in light of the accompanying drawings.

BRIEF DESCRIPTION OF THE DRAWINGS

FIG. 1 is a graph of acetic acid concentration in the aqueous phase as a function of pH resulting from the study described in Example 1.

FIG. 2 is a graph of acetic acid concentration in the aqueous phase as a function of reaction temperature.

FIG. 3 is a graph showing the extent of acetic acid extraction under various TOPO concentrations in undecane.

FIG. 4 is a graph showing partition coefficients as a function of TOPO concentrations in undecane.

DETAILED DESCRIPTION OF THE PREFERRED EMBODIMENT

Unexpectedly, it has been discovered that acetic acid can be effectively recovered from the wood extracts described above by a process using a water insoluble solvent such as undecane containing an extractant such as TOPO. The acetic acid can be recovered either in the acid form or in the salt form as an acetate.

The process includes providing an aqueous wood extract containing acetic acid and dissolved hemicellulose which contains uronic acid. Typically the wood extract contains acetic acid, dissolved monomeric or oligomeric hemicelluloses, and cellulose. The dissolved hemicelluloses contain uronic acids. The wood extract may also contain furfural and other carbohydrate degradation products, methanol derived from wood derived pectins, and methylglucoronic acids. In some embodiments, the wood extract is a product from the treatment of wood chips or lignocellulosic biomass with high temperature steam/water or aqueous solution to release sugars.

The process also includes providing a water insoluble solvent containing an extractant for the acetic acid. Any suitable solvent can be used. For example, the solvent may be selected from the paraffin hydrocarbons, including straight-chain paraffin compounds such as undecane, hexane, heptane, octane, nonane, decane, dodecane, tridecane, tetradecane and pentadecane, branched paraffin compounds such as isooctane, isohexane and isododecane and cyclic paraffin compounds such as cyclohexane. Alternatively, the solvent may be selected from the olefin hydrocarbons, including straight-chain olefin compounds such as hexene, octene, decene, dodecene and tetradecene, branched olefin compounds such as diisobutylene and triisobutylene and cyclic olefin compounds such as cyclohexene and dicyclopentene. Further examples of solvents that may be suitable include aromatic hydrocarbons such as toluene, xylene and cumene, and various terpene type compounds.

The extractant for the acetic acid can be dispersed or dissolved in the water insoluble solvent. Any suitable extractant for acetic acid can be used. For example, solvents with a high distribution coefficient can be used to extract the acetic acid. These include trioctylphosphine oxide (TOPO) and long-chain aliphatic amines (including secondary, tertiary and quaternary amines).

The wood extract is contacted with the solvent and extractant in order to extract the acetic acid from the wood extract. This extraction can be done in any suitable manner. For example, the solvent and extractant can be mixed with the wood extract to extract the acetic acid, and then the solvent, extractant and acetic acid can be separated from the remaining wood extract. In some embodiments, the solvent, extractant and acetic acid become phase separated from the remaining wood extract, allowing them to be easily separated. Any suitable process conditions can be used, some of which are described in the following examples.

Lastly, the acetic acid is recovered from the solvent and extractant. This can be done in any suitable manner. In one example, the acetic acid is recovered by distillation. For example, the high boiling point of TOPO (213° C.) and undecane (196° C.) relative to that of acetic acid (118° C.) allows simple recovery of acetic acid from the TOPO-undecane phase by distillation. Again, any suitable process conditions can be used, some of which are described in the following examples.

EXAMPLE 1

In the experiments described below it is shown that TOPO-undecane is an efficient organic solution to remove acetic acid from sugar solutions obtained by treatment of wood with pure water or green liquor (aqueous solution of mostly $Na_2CO_3$). The results are compared with, and the optimum operating conditions for the extraction process are determined for acetic acid extraction from a pure acetic acid solution.

Materials and Methods

Green Liquor

Green liquor is the liquid obtained after dissolution of the liquid smelt obtained from the bottom of the kraft recovery boiler. It consists mainly of an aqueous solution of $Na_2CO_3$, $Na_2S$, $Na_2SO_4$ and smaller quantities of other alkali metal salts. In this study, pure chemicals ($Na_2S$: Sodium Sulfide hydrate, 65% extra pure, $Na_2CO_3$: Sodium carbonate monohydrate 99.5% extra pure, Fisher, $Na_2SO_4$: Sodium sulfate anhydrous, 99.2% extra pure, NaOH: Sodium hydroxide pellets, 98.5% extra pure, Pittsburgh, Pa.) were used for this study. The composition of the green liquor used in the study is listed in Table 1.

TABLE 1

Chemical Composition of Green Liquor used in Extraction Process

| Chemical | Concentration |
| --- | --- |
| Sodium hydroxide (NaOH) | 9.0 g/l as $Na_2O$ |
| Sodium sulfide ($Na_2S$) | 29.1 g/l as $Na_2O$ |
| Sodium Carbonate ($Na_2CO_3$) | 70.0 g/l as $Na_2O$ |
| Sodium Sulfate ($Na_2SO_4$) | 0.8 g/l as $Na_2O$ |
| TTA (Total Titratable Alkali) | 108.9 g/l as $Na_2O$ |

Green Liquor and Hot Water Extraction

Mixed northeast hardwood chips were used for extraction of hemicelluloses of wood. The most prevalent hardwood species in the mix is maple, with smaller amounts of poplar and birch. The hemicellulose extractions were performed using a 20 L rocking digester at the University of Main Pilot Plant. The digester was loaded with 2 kg (oven dry weight) of fresh chips and mixed with green liquor and water (including wood moisture) at overall liquor to wood ratio of 4:1 L/kg. The green liquor charge on wood is 3%, expressed as grams of $Na_2O$ per 100 gram of dry wood. In the case of extraction with pure water, the same liquor to wood ration was used without any green liquor charge. This system was agitated (2 rpm) at 160° C. for 110 minutes yielding an H-factor of 800 hrs. The reactor was then cooled below 100° C. The free-draining liquor was collected and used for the acetic acid extraction experiments. The composition of the green liquor (GL) and hot water (HW) extracts are shown in Table 2.

TABLE 2

Composition of 3% Green Liquor (GL) and Hot Water (HW) Extracted Northern Hardwood.

| Composition of Extract | GL Extract[2] [g/L] | GL Extract[3] [g/L] | HW Extract[2] [g/L] | HW Extract[3] [g/L] |
| --- | --- | --- | --- | --- |
| Glucose | 0.36 | 0.09 | 1.01 | 0.09 |
| XMG[1] | 1.62 | 0.11 | 9.06 | 0.65 |
| Arabinose | 0.24 | 0.02 | 1.37 | 1.07 |
| Acetic Acid | 9.40 | 8.32 | 3.47 | 1.27 |
| Total Sugars | 2.22 | 0.22 | 11.44 | 1.81 |

Note:
[1]xylose, mannose, and galactose,
[2]secondary hydrolyzed with 72% sulfuric acid,
[3]analyzed without secondary hydrolysis.

Experimental

In this study, trioctylphosphine oxide (TOPO, [$CH_3(CH_2)_7$]3PO, Mol. W. 386.64, ReagentPlus, 99% pure, Fisher), acetic acid ($C_2H_4O_2$, glacial, 99.99+%, Sigma), and undecane ($C_{11}H_{24}$, Mol. W. 156.3, 99+%, Fisher) were purchased. A typical extraction procedure was as follows: 10.0 ml of the aqueous phase containing a certain amount of acetic acid was vigorously shaken with 10.0 ml of the organic phase (undecane containing a certain amount of TOPO) for 36 minutes at various temperatures. Samples of both phases were analyzed immediately after the phase separation using centrifugation. The concentration of acetic acid in the organic phase was determined by 0.05 M NaOH titration of 5 mL of the organic phase using phenolphthalein as indicator. The concentration of acetic acid in the aqueous phase was determined by HPLC.

High Performance Liquid Chromatography

The composition of acetic acid in the aqueous phase was quantitatively analyzed by HPLC with RI detector. A Shimadzu HPLC model LC-10AT with a Bio-Rad Aminex HPX-87H column kept at 60° C. and 5 mM $H_2SO_4$ as eluent at a flow rate of 0.6 mL/min was used. The acetic acid concentration was quantified using a calibration curve prepared with known acetic acid concentrations.

Titration

In extraction experiments involving TOPO, the presence of TOPO in the organic phase precludes the determination of acetic acid by GC due to the deposition of TOPO on the glass insert in the injection port. The titration procedure was, therefore carried out by withdrawing an aliquot from the organic phase, followed by titration with standardized 0.05 M NaOH solution using phenolphthalein as indicator.

Results

Extraction of a Pure Acetic Acid Solution

The effect of pH on the removal of acetic acid from a pure 10 g/L acetic acid solution at 70° C. using TOPO-undecane at a concentration of TOPO of 37% (w/v) is shown in FIG. 1. It can be seen that the removal efficiency of acetic acid from the aqueous phase decreases significantly when the pH is raised above 3. This is to be expected since the pKa of acetic acid is 4.8, and the acetic acid must be in the protonated form for efficient complexation with TOPO.

The effect of temperature on the efficiency of acetic acid extraction is displayed in FIG. 2. It confirms that the optimum operating temperature of the extraction is 70° C.

Extraction of acetic acid from "green liquor" (GL) and hot water (HW) wood extracts The equilibrium data for extraction of acetic acid from the two types of wood extracts is given in Table 3. It shows that about 60% of the acetic acid in the acidified (pH=1) GL extract is transferred to the organic phase (TOPO-undecane) containing 37% w/v TOPO when the GL extract is treated with an equal volume of TOPO-undecane at 70° C. for 36 minutes. This is equivalent to a partition coefficient of 2.0 g/g. The same partition coefficient is also found for the hot water (HW) extract at the same acetic acid extraction operating conditions. This shows that surprisingly the presence of the other organic acids, sugars, other organics and the inorganic salts do not interfere with the acetic acid extraction. The phase separation after TOPO-undecane extraction of the aqueous acetic acid solution and the HW and GL extracts was observed. This confirms that the presence of the organics in the HW and GL extracts do not prevent good phase separation.

TABLE 3

Equilibrium Data for Extraction of Acetic Acid from Green Liquor (GL) and Hot Water (HW) extract with TOPO-Undecane.

| TOPO conc. in Undecane | Acetic acid conc. of GL extract [g/L] | | Acetic acid conc. of HW extract [g/L] | | Partition coefficient, $P_c$ [org/aq] | | Recovery acetic acid in org phase [%, g/g] | |
|---|---|---|---|---|---|---|---|---|
| [%, w/v] | aq[1] | org[2] | aq | org | GL extract | HW extract | GL extract | HW extract |
| 5 | 5.25 | 1.65 | 1.10 | 0.09 | 0.31 | 0.08 | 19.8 | 7.1 |
| 9 | 4.12 | 2.97 | 0.78 | 0.21 | 0.72 | 0.28 | 35.7 | 17.0 |
| 18 | 2.98 | 3.96 | 0.57 | 0.48 | 1.33 | 0.84 | 47.6 | 37.8 |
| 28 | 2.51 | 4.35 | 0.55 | 0.65 | 1.73 | 1.19 | 52.3 | 51.5 |
| 37 | 2.43 | 4.95 | 0.31 | 0.63 | 2.04 | 2.03 | 59.5 | 49.6 |
| 46 | 2.23 | 5.22 | 0.30 | 0.71 | 2.34 | 2.39 | 62.8 | 56.5 |
| 55 | 2.04 | 5.34 | 0.27 | 0.66 | 2.62 | 2.46 | 64.2 | 52.2 |

Note:
Initial concentration of acetic acid: GL extract (8.32 g/L), HW extract (1.27 g/L).
Conditions: pH = 1, temperature = 70° C., and residence time = 36 minutes.
Ratio of TOPO-undecane and GL or HW samples = 1:1 (v/v).
[1]aqueous phase.
[2]organic phase.

The extractions with TOPO-undecane of the three extracts at different concentrations of TOPO are compared in FIG. 3. It confirms that the extraction efficiency of the acetic acid is essentially the same for the GL extract as that for an aqueous solution of pure acetic acid.

The partition coefficient for the extraction of the pure acetic acid solution experiments shown in FIG. 3 are displayed in FIG. 4. It shows that the concentration of TOPO in undecane should be raised to 37% (w/v) to achieve a partition coefficient of 2.0; i.e. the same result as that obtained for the GL and HW extracts at the same acetic acid extraction operating conditions as presented earlier in Table 3.

EXAMPLE 2

A solution was prepared containing 10 g/l acetic acid, 10 g/l glucuronic acid (Sigma Aldrich; CAS number 6556-12-3; product number G5269-10G), 5 g/l glucose, 20 g/l xylose and 0.3 g/l furfural. This is called solution A and is representative of a wood extract. Solution B was prepared containing 10 g/l acetic acid and 0.3 g/l furfural. This solution is representative of an evaporator condensate when concentrating an acidified wood extract or acid sulfite pulping liquor. The pH of both solutions was adjusted to 2 using sulfuric acid.

5 ml of the solutions were pipetted into 10 ml reaction vessels, heated to 70° C. and mixed with 5 ml of TOPO/n-undecane (1/2). A batch extraction was performed by vigorously shaking the vessels for 7 seconds, followed by several minutes in a thermostat bath of 70° C. The shaking/thermostating was repeated six times.

After the extraction, the phases were separated by centrifugation and the remaining aqueous phase was analyzed. The results are summarized in Table 4.

TABLE 4

Analysis of Aqueous Phase

| compound | glucuronic acid conc. (mg/l) | acetic acid conc. (mg/l) | acetic acid recovery (%) | glucose conc. (mg/l) | xylose conc. (mg/l) | furfural conc. (mg/l) | furfural recovery (%) |
|---|---|---|---|---|---|---|---|
| solution A | 10655 | 10050 | | 4913 | 20090 | 291 | |
| extraction 1 | 10678 | 4977 | 49.5 | 5020 | 20345 | 114.7 | 39.4 |
| extraction 2 | 10742 | 4925 | 49.0 | 5030 | 20258 | 110 | 37.8 |
| mean | 10710 | 4951 | 49.3 | 5025 | 20302 | 112.4 | 38.6 |
| solution B | | 10045 | | | | 292 | |
| extraction 1 | | 4653 | 46.3 | | | 120.8 | 41.4 |
| extraction 2 | | 4504 | 44.8 | | | 118.6 | 40.6 |
| mean | | 4579 | 45.6 | | | 119.7 | 41.0 |

The results show that the acetic acid extraction efficiency decreases from 54.5% for solution B (representing the wood extract) to 50.7% for solution A (representing the evaporator condensate), whereas the furfural extraction efficiency increases from 59.0% to 61.4% respectively. These results also show that no extraction of glucuronic acid, xylose or glucose takes place. As a matter of fact, the concentrations of glucuronic acid, xylose and glucose increase by respectively 0.5, 1.1 and 2.3%, suggesting that the increase in the concentration of glucuronic acid, xylose and glucose is due to evaporation of water during handling of the 70° C. water phase, and not due to loss of water since the solubility of water in n-undecane is quite poor (130 mg/kg at 40° C.). Thus the extraction of glucuronic acid is minimal, and accumulation of glucuronic acid moieties over time in the TOPO/undecane will not occur.

In summary these tests show that the process of the invention will work on a hydrolyzed and filtered (lignin and colloidal material removed) wood extract containing monosugars, acetic acid, glucuronic acid and furfural.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A process for recovering acetic acid from a wood extract comprising:
   providing an aqueous wood extract containing acetic acid and dissolved hemicellulose containing uronic acid;
   providing a water insoluble solvent containing an extractant for the acetic acid;
   contacting the wood extract with the solvent and extractant in order to extract the acetic acid from the wood extract; and
   recovering the acetic acid from the solvent and extractant.

2. The process of claim 1 wherein the extractant for acetic acid comprises a solvent with a high distribution coefficient.

3. The process of claim 2 wherein the extractant for acetic acid comprises trioctylphosphine oxide.

4. The process of claim 1 wherein the water insoluble solvent comprises a paraffin hydrocarbon.

5. The process of claim 4 wherein the water insoluble solvent comprises undecane.

6. The process of claim 1 wherein the wood extract further contains organic acid.

7. The process of claim 6 wherein the wood extract is a product from the treatment of wood chips or lignocellulosic biomass with high temperature steam/water or aqueous solution to release sugars.

8. The process of claim 1 wherein the contacting step comprises mixing the solvent and extractant with the wood extract to extract the acetic acid, and then separating the solvent, extractant and acetic acid from the remaining wood extract.

9. The process of claim 1 wherein the acetic acid is recovered from the solvent and extractant by distillation.

10. The process of claim 1 wherein the extractant for acetic acid comprises trioctylphosphine oxide, the water insoluble solvent comprises undecane, and the wood extract is a product from the treatment of wood chips or lignocellulosic biomass with high temperature steam/water or aqueous solution to release sugars.

* * * * *